(12) United States Patent
Mathur et al.

(10) Patent No.: US 12,168,762 B2
(45) Date of Patent: Dec. 17, 2024

(54) PROCESS FOR PRODUCTION OF ENRICHED ALGAL BIOMASS

(71) Applicants: Indian Oil Corporation Limited, Maharashtra (IN); Department of Biotechnology, New Delhi (IN)

(72) Inventors: Anshu Shankar Mathur, Haryana (IN); Preeti Mehta, Haryana (IN); Rekha Rani, Haryana (IN); Ankita Kandpal, Haryana (IN); Ravi Prakash Gupta, Haryana (IN); Suresh Kumar Puri, Haryana (IN); Sankara Sri Venkata Ramakumar, Haryana (IN)

(73) Assignees: Indian Oil Corporation Limited, Mumbai (IN); Department of Biotechnology, New Delhi (IN)

( * ) Notice: Subject to any disclaimer, the term of this patent is extended or adjusted under 35 U.S.C. 154(b) by 0 days.

(21) Appl. No.: 17/987,515

(22) Filed: Nov. 15, 2022

(65) Prior Publication Data
US 2023/0151323 A1    May 18, 2023

(30) Foreign Application Priority Data
Nov. 15, 2021   (IN) .............................. 202121052370

(51) Int. Cl.
*C12N 1/12*     (2006.01)
*C12R 1/89*     (2006.01)

(52) U.S. Cl.
CPC .......... *C12N 1/125* (2021.05); *C12R 2001/89* (2021.05)

(58) Field of Classification Search
CPC ...... C12N 1/125; C12N 1/12; C12R 2001/89; C12P 7/6436; C12P 7/6463; C12P 7/6472; C12P 7/649; A01G 33/00
See application file for complete search history.

(56) References Cited

U.S. PATENT DOCUMENTS

| | | |
|---|---|---|
| 8,124,384 B2 | 2/2012 | Bailey et al. |
| 9,434,898 B2 * | 9/2016 | Raney ........................ C11B 1/00 |
| 9,848,623 B2 | 12/2017 | Bailey et al. |
| 9,890,402 B2 | 2/2018 | Mathur et al. |
| 10,351,814 B2 | 7/2019 | Delaroche et al. |
| 10,570,427 B2 * | 2/2020 | Simpson ............... C12P 7/6472 |
| 2008/0038774 A1 | 2/2008 | Higashiyama et al. |
| 2011/0091945 A1 | 4/2011 | Das et al. |
| 2016/0244789 A1 * | 8/2016 | Mathur ................. C12P 7/6427 |
| 2016/0298149 A1 | 10/2016 | Caulier |

FOREIGN PATENT DOCUMENTS

| | | | |
|---|---|---|---|
| WO | WO2001054510 A1 | 8/2001 | |
| WO | WO-2007068997 A2 * | 6/2007 | ............... C11B 1/10 |
| WO | WO2008049512 A1 | 5/2008 | |
| WO | WO2015068896 A1 | 5/2015 | |

OTHER PUBLICATIONS

Ahmad et al. African Journal of Environmental Science and Technology, 7, 358-365 (Year: 2013).*
Pawar et al. Bioresource Technology, 2021, 325, 124636 (Year: 2021).*
Chen et al. Bioresource Technology, 2017, 244, 1198-1206 (Year: 2017).*
Awad D, Bohnen F, Mehlmer N and Brueck T (2019), "Multi-Factorial-Guided Media Optimization for Enhanced Biomass and Lipid Formation by the Oleaginous Yeast Cutaneotrichosporon oleaginosus", Frontiers in Bioengineering and Biotechnology, vol. 7, Article 54. doi: 10.3389/fbioe.2019.00054.
Chen et al., "Improvement in the docosahexaenoic acid production of Schizochytrium sp. S056 by replacement of sea salt", Bioprocess Biosyst Eng (2016) 39:315-321, DOI 10.1007/s00449-015-1517-1.
Andrea Meo Xenia Laura Priebe Dirk Weuster-Botz, "Lipid production with Trichosporon oleaginosus in a membrane bioreactor using microalgae hydrolysate", http://dx.doi.org/doi:10.1016/j.jbiotec.2016.10.021.
Mlíckova et al., "Lipid Accumulation, Lipid Body Formation, and Acyl Coenzyme a Oxidases of the Yeast Yarrowia lipolytica", Applied and Environmental Microbiology, Jul. 2004, p. 3918-3924, DOI: 10.1128/AEM.70.7.3918-3924.2004.
Naduthodi et al., "Progress of CRISPR-Cas based genome editing in Photosynthetic microbes", doi: [10.1002/biot.201700591]. 2018.
Shahid et al., "Engineering the metabolic pathways of lipid biosynthesis to develop robust microalgal strains for biodiesel production", DOI: 10.1002/bab.1812, Published online 0 xxxx 2019 in Wiley Online Library (wileyonlinelibrary.com).
Sharma PK, Saharia M, Srivstava R., Kumar S. and Sahoo L. (2018), "Tailoring Microalgae for Efficient Biofuel Production", Frontiers in Marine Science, 5:382, doi: 10.3389/fmars.2018.00382.

* cited by examiner

*Primary Examiner* — Jennifer M.H. Tichy
*Assistant Examiner* — Lioubov G Korotchkina
(74) *Attorney, Agent, or Firm* — Blank Rome LLP

(57) ABSTRACT

The present invention relates to a process for producing enriched algal biomass having high lipid productivity. More particularly, the present invention provides a process for obtaining an enriched biomass with omega-3 fatty acids by using a microalgal strain *Schizochytrium* MTCC 5890 in a unique media composition and substrate residual band in a steady state continuous fermentation. The process of the present invention results in high biomass and lipid productivity.

8 Claims, 4 Drawing Sheets

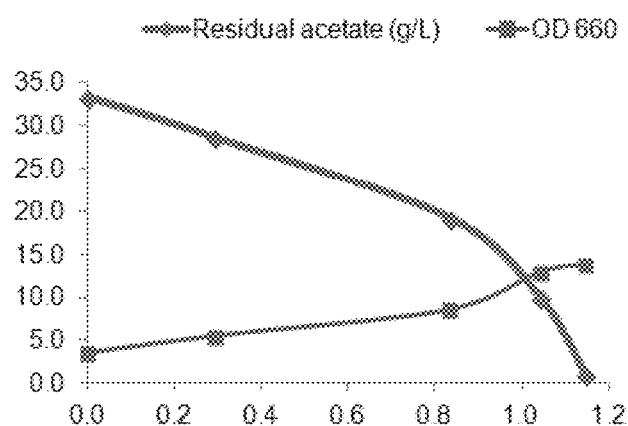
Fig. 1A
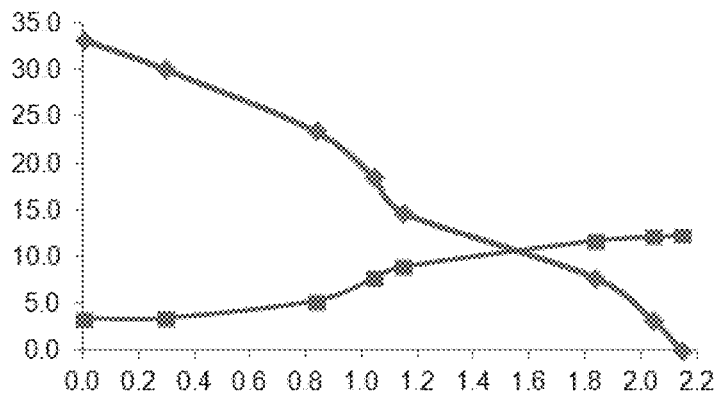
Fig. 1B
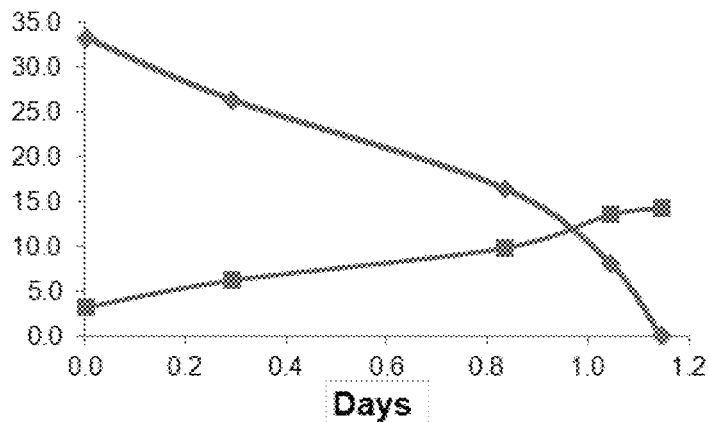
Fig. 1C
Figure 1

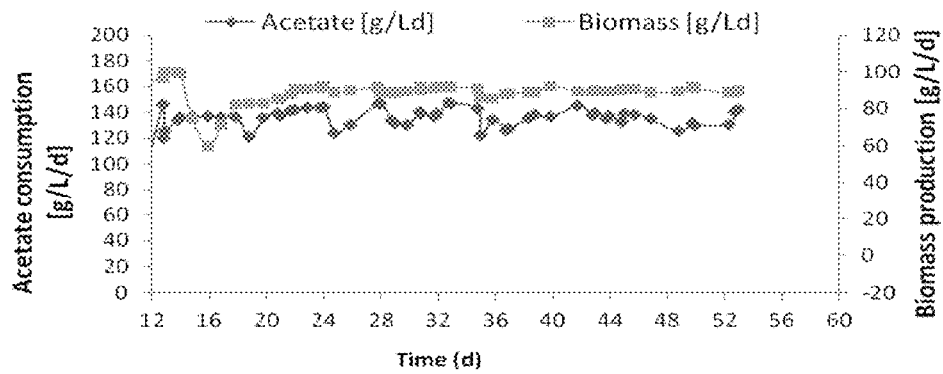
Fig. 4A
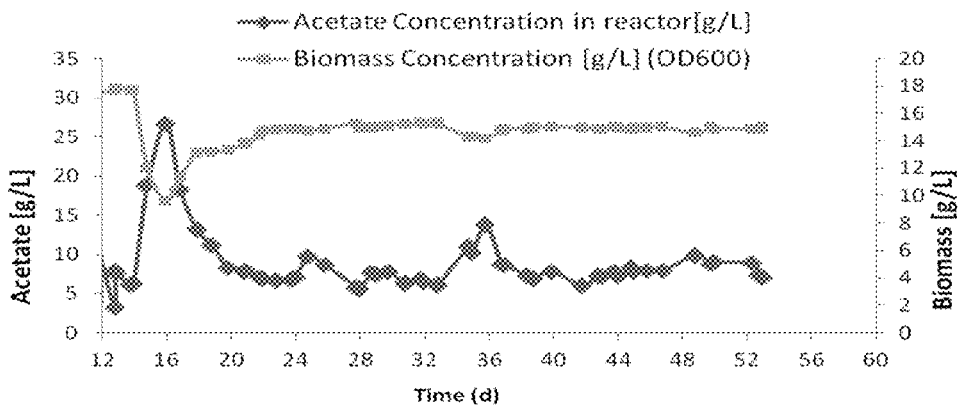
Fig. 4B
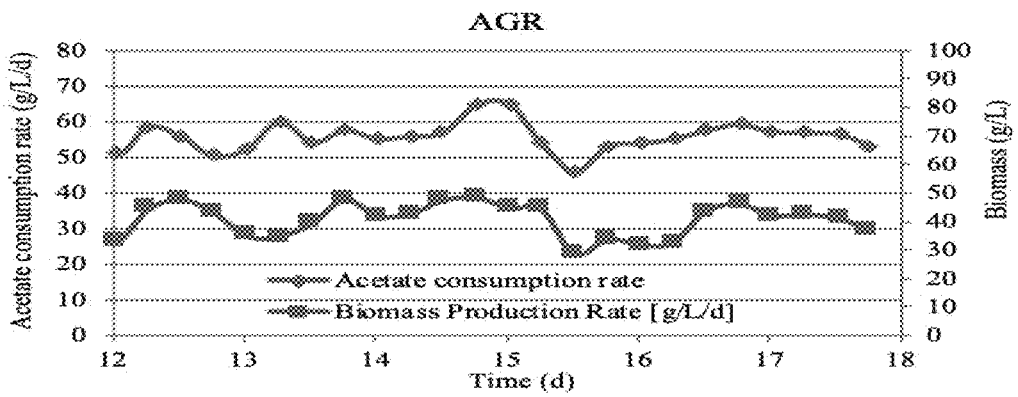
Fig. 4C
Figure 4

PROCESS FOR PRODUCTION OF ENRICHED ALGAL BIOMASS

RELATED APPLICATION

This application claims the benefit of Indian application No. 202121052370, filed on Nov. 15, 2021. The entire disclosure of this application is hereby incorporated by reference.

FIELD OF THE INVENTION

The present invention relates to a process for producing enriched algal biomass having high lipid productivity. More particularly, the present invention provides a process for obtaining enriched biomass with omega-3 fatty acids by using a microalgal strain in a unique media composition and substrate residual band in a steady state continuous fermentation. The process of the present invention results in high biomass and lipid productivity.

BACKGROUND OF THE INVENTION

Microbial biomass derived biofuels have emerged as front runner to address the conventional and bio-energy crops-based problems. The cultivation of oleaginous microorganisms for biodiesel application offers a commercial and sustainable edge over oil crops. The commercial success of oleaginous organisms for biodiesel production relies upon various factors such as high biomass and lipid productivity, using cheap raw material and co-products credits, to make the process cost effective as compared to conventional fuels. To that end, Thraustochytrids offers a potentially sustainable option to meet the demand for biobased energy along with concurrent production of high value-added co-products such as long chain polyunsaturated fatty acids i.e., omega-3-fatty acids. These organisms can convert a broad spectrum of waste substrates in to high value-added lipids along with triglycerides for biodiesel and make algal biofuel production cost effective and environmentally sustainable. Thraustochytrids are commercially recognized to produce several nutraceutical and functional food compounds including polyunsaturated omega-3 fatty acids, carotenoids, sterols, exopolysaccharides and enzymes. Omega-3 fatty acids and especially docosahexaenoic acid (DHA) are essential fatty acids which have multiple health benefits associated with developmental and maintenance of ocular, brain and heart tissues and muscles. These fatty acids are reported to reduce inflammation, atherosclerosis, high cholesterol, high blood pressure etc. Escalating consumer awareness about the health benefits of omega-3 has significantly contributed to the growth of the omega-3 market. The omega-3 market is expected to grow at a CAGR of 13.1% to reach USD 8.52 billion by 2025 from 4.07 billion in 2019 (https://www.marketsandmarkets.com/Market-Reports/omega-3-omega-6-227.html). Though cultivation of such oleaginous microbes are commercially for food, feed and neutraceutical is a proven technology, however there are still various impediments associated with the process cost that needs to be further reduced for commercial viability. To that end, several strategies such as innovative fermenter designs, utilization of industrial waste streams, suitable nutrient medium, robust strains could be implemented to improve the overall process productivity and viability (Awad 2019, Mathur et al., 2018, Shahid et al., 2019, Meo et al., 2017, Caulier et al., 2016, Higashiyama et al., 2008). Strategies to maximize the overall productivity i.e., biomass and lipid production are pivotal for improving the economics of microalgae-based industries.

Previous work on enhancement of biomass and lipid production were attempted using genetic engineering to improve the substrate uptake and modification in the metabolic flux into lipogenic pathways, thereby improving lipid productivity under nutrient limitation condition and tailor process specific FA profiles (Mlickova et al., 2004, Sharma et al., 2018). Some of the known previous arts suggested homologous recombination or random insertion mutations, molecular modifications of the genes of microalgae, CRISPR-associated transposase technology to improve the productivity of lipids (Shahid et al., 2019). However, there are no efficient gene editing methods, lack of functional annotations and absence of proteomic data for all oleaginous strains remains a challenge in most species (Naduthodi et al., 2018). Moreover, genetic manipulation leads to inheritable changes in a species that might affect the ecosystem adversely, when used for environmental and agricultural applications.

The enhancement of biomass and/or lipid using various growth promoters, phytohormones and micronutrients was also reported (US Patent US2011/0091945A1). However, previous patents disclosed the method of improving the content of total lipid in later stage of growth wherein N-stress was introduced which results in the cessation of cell growth and an overall reduction in lipid productivity. Previous studies mainly focussed on improving the fermentation strategies which include membrane based two stage lipid production process from organic acid produced during gas fermentation and aerobic fermentation (Mathur et al., 2018, Simpson et al., 2020) or exploitation of various fermentation strategies such as oxygen control method (U.S. Pat. Nos. 9,848,623 B2, 1,035,1814B2, US2016/0298149A1 and U.S. Pat. No. 8,124,384B2) i.e. the lower dissolved oxygen during lipid production stage in the absence of nitrogen and high dissolved oxygen during the biomass density increasing stage. The high mixing and aeration for maintaining high dissolved oxygen can easily lead to severe foaming and cells shearing. However, the scalability of these bioprocesses at industrial scale demands more cost and energy. These technologies have reached a point where the lipid and biomass productivity of microalgae cannot be further improved using only fermentation optimizations. Thereby, the extensive development of culture techniques including the search for more inexpensive culture medium and trace nutrients, the method of regulating the starter culture to improve the substrate utilization and biomass productivity is indispensable.

Thraustochytrids are exclusively marine microbes, cultivated in media having seawater or sea salt. Identifying and designing optimal growth medium compositions plays a crucial role in the development of commercial process. Carbon, nitrogen and macronutrients are regarded as most crucial elements in the medium. Conventional approaches to improve product yield and volumetric productivities of Thraustochytrid mainly involves manipulation of nutritional (e.g., nitrogen, phosphorus and sea salt) and environmental (e.g., temperature, pH and salinity etc.) factors (US2011/0091945). As a strategy for technological development, the replacement of sea salt or seawater with sodium chloride and sodium sulphate are being investigated (Chen et al., 2016, Mathur et al., 2018). However, the addition of sea water, sea salt, sodium chloride and sodium sulphates are reported to corrode the commercial scale reactors in long term operations. Thus, there are various reports on media formulations with the addition of various ions such as potassium, sodium, calcium, magnesium and phosphoric acid without the inclusion of sea salt, sodium chloride and sodium sulphates (Higashiyama et al., 2004). Previous work on the enhancement of biomass and lipids were attempted using carbon to nitrogen ratio (C:N) wherein lipid yield in addition to biomass formation was influenced by C:N ratio (Awad et al., 2019). On the other hand, there are no reports that investigated the effect of more aggressively enhancing the productivity of biomass by increasing substrate utilization efficiency by optimizing the particular ratio of major ions such as potassium and magnesium to nitrogen (i.e., K/N, Mg/N etc) and no reports that even investigates the effect which the balance of added of major ion to nitrogen ratio on biomass and lipid compositions.

Further, in prior arts, most conventional studies were done to increase biomass productivities have focused on strain selection, genetic modification, manipulation of nutritional (especially carbon to nitrogen ratio) factors, optimization of various fermentation strategies, supplementation of growth promoters, phytohormones and micronutrients etc. However, till now, there has been no reports that investigated the effect of more aggressively enhancing the productivity of biomass by increasing substrate utilization efficiency and dilution in continuous fermentations by adding and maintaining defined concentrations of major ions such as potassium and magnesium and nitrogen and substrate in a well-balanced ratio.

WO2001054510A1 discloses a process for producing lipids containing polyenoic fatty acids from eukaryotic microorganism capable of producing at least about 20% of their biomass as lipids comprising adding to a fermentation medium comprising said microorganisms a non-alcohol carbon source and a limiting nutrient source at a rate sufficient to increase the biomass density of said fermentation medium to at least about 100 g/L.

WO 2008/049512 A1 relates to improved methods for production of omega-3 fatty acids by microorganisms belonging to the microflora of Thraustochytriales using a modified composition of the culture medium. Further, the document describes a process for production of omega-3 fatty acids by culturing microflora, such as strains of *Ulkenia*, *Thraustochytrium* and/or *Schizochytrium*, in fermentors which includes the step of culturing the Thraustochytriales microflora in an environment of reduced sodium ions and increased potassium ions.

WO 2015/068896A1 relates to a new *Micractinium inermum* NLP-F014 KCTC 12491BP microalgae capable of producing biofuels and their use. Further, it provides a biomass fuel comprising the microcavity *Micractinium inermum* NLP-F014 KCTC 12491BP microalgae or a culture thereof.

US 2016/0244789 A1 provides a thraustochytrid based process for treating waste effluents in a continuous process of sequestration of nutrients from discharge of gas fermentation plants and its biotransformation in value added products such as high value omega-3 fatty acids and lipids for biodiesel.

Although, available literature provides several methods for enhancing algal biomass, however none of these methods provides a method of adding ions with respect to nitrogen for enhancing biomass without decreasing the lipid content. Thus, the present invention addresses the above problems and provides a novel method for increasing the biomass and lipid productivities or cell population by contacting the cell population with chemical compounds in unique proportion that are capable of increasing the volumetric productivity and nutrient sequestration ability of microalgal strain.

SUMMARY OF THE INVENTION

In an aspect of the present invention, there is provided an improved process for production of enriched algal biomass having high lipid productivity, the process comprising of:
i. providing an active starter culture of a microalgal strain;
ii. inoculating 10% v/v of the microalgal strain of step (i) in a nutrient medium in fermentor with a substrate, wherein in the nutrient media, the ratio of K/N:Mg/N:Cu/N is 0.349:0.109:0.023;
iii. fermenting the medium of step (ii) at a temperature ranging from 20-37° C. at aeration of 0.75-1 v/v/min and stirring regulated in the range from 150 to 900 rpm to keep dissolved oxygen at 20% through out in long continuous run;
iv. maintaining pH value of the medium of step (iii) in the range of 6.5-9.5 and concentration of residual substrate in the range of 4-15 g/L inside the fermentor;
v. allowing the culture to grow in logarithmic phase in a steady state continuous run; and
vi. obtaining high productivity of algal biomass enriched with omega-3 containing lipids from the fermentor.

In an embodiment of the present invention, there is provided a process, wherein the microalgal strain is *Schizochytrium* MTCC 5890.

In another embodiment of the present invention, there is provided a process wherein the substrate is acetate.

In yet another embodiment of the present invention, there is provided a process wherein acetate is used in the concentration of 30 g-40 g/L.

In still another embodiment of the present invention, there is provided a process wherein the nutrient media is a modified minimal base media.

In an embodiment of the present invention, there is provided a process wherein the pH value of the medium is maintained by adding sulphuric acid.

In another embodiment of the present invention, there is provided a process wherein the obtained biomass and lipid productivity is in the range of 80-90 g/L/day and 20-30 g/L/day.

In another aspect of the present invention, there is provided a nutrient media for enhancing algal biomass and lipid productivity comprising acetate as substrate in the range of 30-40 g/L, potassium ($K^+$) ions in the range of 5-150 mM, magnesium ($Mg^{2+}$) in the range of 4-10 mM, copper (Cu) ions in the range of 0.4-0.9 mM, calcium ($Ca^{2+}$) ions in the range of 0.3 mM-0.9 mM, sulphate ($SO_4$) in the range of 5.6-15 mM, urea in the range of 14 mM-40 mM, trace elements selected from $FeCl_3$, $CoCl_2$, $H_3BO_3$, $Na_2MoO_4$, $ZnCl_2$, $Na_2WO_4$ and vitamins selected from biotin, folic acid, pyridoxine·HCl, thiamine·HCl, riboflavin, nicotinic acid, B12 and thioctic acid.

In an embodiment of the present invention, there is provided a process wherein the media is a modified minimal base media.

In another embodiment of the present invention, there is provided a process wherein the ratio of K/N:Mg/N:Cu/N in the medium is 0.349:0.109:0.02.

These and other features, aspects, and advantages of the present subject matter will be better understood with reference to the following description. This summary is provided to introduce a selection of concepts in a simplified form.

BRIEF DESCRIPTION OF DRAWINGS

These and other features, aspects, and advantages of the present invention will become better understood when the following detailed description is read with reference to the accompanying drawings in which like characters represent like parts throughout the drawings wherein:

FIG. 1 illustrates the growth and substrate consumption of *Schizochytrium* MTCC 5890 in complex medium (FIG. 1A), minimal BM medium (FIG. 1B) and modified MBM medium (FIG. 1C).

FIG. 4 illustrates the changes in biomass and acetate consumption rate in modified media (FIG. 4A) and (FIG. 4B) and in control (FIG. 4C) in continuous fermentation. Control means minimal media not supplemented with additional potassium, magnesium and copper.

DETAILED DESCRIPTION OF THE INVENTION

Figure 2:
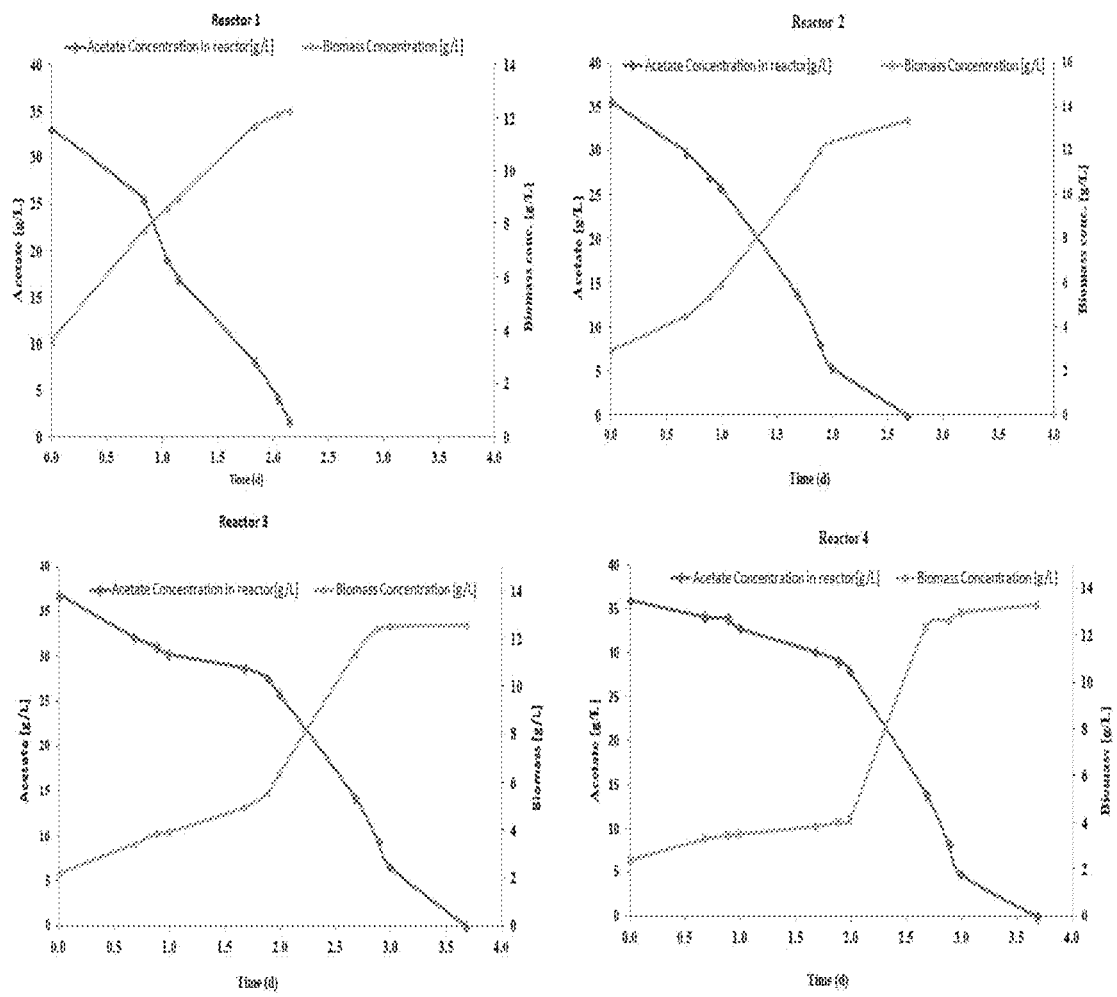
FIG. 2 illustrates the growth kinetics and optimum residual substrate concentration using modified MBM medium in four batch parallel reactors.

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

Definition

For the purposes of this invention, the following terms will have the meaning as specified therein:

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to" "including" and "including but not limited to" are used interchangeably.

The present invention provides a method for enhancing/enriching the production of algal biomass and thus high lipid productivity. The method is comprising: a highly active starter inoculum with a composition selected to enhance the potential of nutrient utilization ability of the culture; and allowing the multifold increment in cell densities/productivities superior to those of conventionally used starter cultures and thereafter continuing the fermentation by allowing the culture to grow much faster with enhanced substrate utilization and productivities in a steady state continuous fermentation by maintaining specific growth rate, controlling residual substrate band concentrations and a unique K/N, Mg/N ratio in a fermentor. Particularly, the present invention relates to a process to enhance nutrient sequestration rate, thus leading to high performing strains and process which leads to increased productivity of the process.

Therefore, the present invention provides a process which improves conventional method of culturing Thraustochytrids, promotes rapid logarithmic cell growth phase and biosynthesis of omega-3 fatty acids so markedly as to enable efficient production of biomass for high value lipids from the culture. Accordingly, in order to attain this objective, *Schizochytrium* MTCC 5890 is cultured with an appropriate and optimized ratio of potassium, magnesium to organic nitrogen source and copper concentration being used in a medium at an K/N ratio of 40% or less, preferably 37% or less, more preferably 34% or less, and Mg/N ratio of 18% or less, preferably 14% or less, more preferably 11% or less to obtain high densities of algal cells in which omega-3 containing lipids have been accumulated. The fermentation is continued wherein the said culture is exposed to the unique selected medium composition and maintaining fixed band of residual steady state concentrations of substrate (substrate concentration 14 g/L or less, preferably 10 g/L or less, more preferably 7 g/L or less) where the potential of culture to provide biomass enriched with high value lipid or biofuel product is enhanced compared to when the culture is not in contact with this unique media composition and substrate residual band in steady state continuous fermentation.

Thus, in accordance with the present invention, there is provided an improved process for production of enriched algal biomass having high lipid productivity, the process comprising of:
 i. providing an active starter culture of a microalgal strain;
 ii. inoculating 10% v/v of the microalgal strain of step (i) in a nutrient medium in fermentor with a substrate, wherein in the nutrient media, the ratio of K/N:Mg/N:Cu/N is 0.349:0.109:0.023;
 iii. fermenting the medium of step (ii) at a temperature ranging from 20-37° C. at aeration of 0.75-1 v/v/min and stirring regulated in the range from 150 to 900 rpm to keep dissolved oxygen at 20% through out in long continuous run;
 iv. maintaining pH value of the medium of step (iii) in the range of 6.5-9.5 and concentration of residual substrate in the range of 4-15 g/L inside the fermentor;
 v. allowing the culture to grow in logarithmic phase in a steady state continuous run; and
 vi. obtaining high productivity of algal biomass enriched with omega-3 containing lipids from the fermentor.

In an embodiment of the present invention, there is provided a process wherein the microalgal strain is *Schizochytrium* MTCC 5890. The *Schizochytrium* MTCC 5890 was isolated from Zuari-Mandovi mangroves, in Goa, India (S15°29'57.39",E73°52'6.13") near the Arabian Sea.

In another embodiment of the present invention, there is provided a process wherein the substrate is acetate.

In yet another embodiment of the present invention, there is provided a process wherein acetate is used in the concentration of 30 g-40 g/L.

In still another embodiment of the present invention, there is provided a process wherein the nutrient media is a modified minimal base media.

In an embodiment of the present invention, there is provided a process wherein the pH value of the medium is maintained by adding sulphuric acid.

In another embodiment of the present invention, there is provided a process wherein the obtained biomass and lipid productivity is in the range of 80-90 g/L/day and 20-30 g/L/day.

In another aspect of the present invention, there is provided a nutrient media for enhancing algal biomass and lipid productivity comprising acetate as substrate in the range of 30-40 g/L, potassium ($K^+$) ions in the range of 5-150 mM, magnesium ($Mg^{2+}$) in the range of 4-10 mM, copper (Cu) ions in the range of 0.4-0.9 mM, calcium ($Ca^{2+}$) ions in the range of 0.3 mM-0.9 mM, sulphate ($SO_4$) in the range of 5.6-15 mM, urea in the range of 14 mM-40 mM, trace elements selected from $FeCl_3$, $CoCl_2$, $H_3BO_3$, $Na_2MoO_4$, $ZnCl_2$, $Na_2WO_4$ and vitamins selected from biotin, folic acid, pyridoxine. HCl, thiamine. HCl, riboflavin, nicotinic acid, B12 and thioctic acid.

The medium composition in grams used in the present process is acetate 30-40 g/L, $MgSO_4 \cdot 7H_2O$: 1.22 g/L, $K_2SO_4$=0.87 g/L, $CaCl_2$)=0.073 g/L, Nitroloacetic acid=0.1 g/L, Phosphoric acid 85%=375 microlitre, $CuSO_4$=400 micro molar, Trace metals added from 0.1M stocks: $FeCl_3$ 10 mL, $CoCl_2$ 1 mL, $H_3BO_3$ 1 mL, $Na_2MoO_4$ 0.1 ml, $ZnCl_2$ 1 mL, $Na_2WO_4$ 0.1 mL, Vitamins stock: Biotin 20 mg, folic acid 20 mg, Pyridoxine. HCl 10 mg, Thiamine. HCl 50 mg, Riboflavin 50 mg, Nicotinic acid 50 mg, B12 50 mg, Thioctic acid 50 mg.

In an embodiment of the present invention, the medium is a modified minimal base medium. In another embodiment of the present invention, the ratio of K/N:Mg/N:Cu/N in the medium is 0.349:0.109:0.02.

The nutrient medium disclosed in the present invention has the advantage of producing biomass and lipid at high yields in an inexpensive manner.

Thus, the process disclosed in the present invention showcases successful implication of specific ions to nitrogen ratio optimization strategy for multi-fold enhancement of biomass and lipid yield for sustainable production of lipids rich with omega-3-fatty acids along with lipids for biodiesel as a renewable fuel. The process includes continual replacement, removal and supplementation of chemical components of the medium, adaptation of starter culture in low cost minimal medium and determination of specific band of concentration of residual substrate in continuous fermentation for enhanced growth, nutrient utilization and biomass productivity. Moreover, the present invention is based, at least in part, on the use of continuous process to identify a band of residual substrate concentration that increase growth rate, yields and productivities in process. Enhancing the biomass productivity from 30-40 g/L/day to 75-90 g/L/day in our existing process will greatly reduce the cost of production of biomass and increase the economic viability of biofuels producing from oleaginous microbes. In addition, the process will significantly increase the profitability of industries producing omega-3-fatty acid biomass for production of food, feed, nutraceutical and pharmaceutical products.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods, the exemplary methods, devices and materials are described herein. It is to be understood that this disclosure is not limited to particular methods, and experimental conditions described, as such methods and conditions may vary.

Example 1: Preparation of Active Starter Culture in Minimal Growth Medium

The economics of large-scale fermentation processes largely depends on media components as they can account for up to 30% of the total production cost. Complex medium components, such as yeast extract and sea salt would cause large variations in process. The exact composition of yeast extract is not actually known because of variations in hydrolysis methods of yeast cells and their composition may vary from one batch to the other and from one company to the other. The presence of NaCl in sea salt in the culture media poses a significant problem of corrosion of fermenters and disposal of effluent. Therefore, it is highly desirable to reduce and/or omit yeast extract and seasalt (chloride specifically) in the culture media to levels at which corrosion is minimal and, at the same time, provide conditions enabling the optimal growth, yield of cultured organisms and consistent replicability. Accordingly, for optimizing the concentration of the minimal medium components for the improvement in reproducibility, growth and yield of the starter culture, three fermentation vessel A, B, C were set up containing complex Yeast Peptone Acetate medium (YPM), minimal medium from gas fermentation waste effluents (BM) and modified minimal medium (MBM). The MBM media was implemented in the study after certain modification of BM medium with supplementation of copper, additional quantity of potassium, magnesium and other trace metals, replacement of sulfates and urea with chlorides and ammonium, respectively.

Medium composition of YPM is acetate 30 g/L, yeast extract 10 g/L, peptone 1 g/L, seasalt 18 g/L. The composition of BM is acetate 30 g/L, $K^+$ ions 2.1 mM, $Mg^{2+}$ 1.9 mM, $Ca^{2+}$ 0.5 mM, $Cl^-$ 25.61 mM, $NH_4Cl$ 19.98 mM, Trace metals added from 0.1M stocks: $FeCl_3$ 10 mL, $CoCl_2$ 1 mL, $H_3BO_3$ 1 mL, $Na_2MoO_4$ 0.1 ml, $ZnCl_2$ 1 mL, $Na_2WO_4$ 0.1 mL, vitamins stock: Biotin 20 mg, folic acid 20 mg, Pyridoxine. HCl 10 mg, Thiamine. HCl 50 mg, Riboflavin 50 mg, Nicotinic acid 50 mg, B12 50 mg, Thioctic acid 50 mg.

The composition of MBM medium is: acetate 30 g/L, K/N:Mg/N:Cu/N:0.349:0.109:0.023 respectively, wherein $K^+$ ions 5-150 mM, $Mg^{2+}$ 4-10 mM, Cu: 0.4-0.9 mM, $Ca^{2+}$ 0.5 mM, $SO^{4-}$ 5.6-15 mM, Urea 39.98 mM, trace metals and vitamins were added same as in BM media.

The medium in the vessels was inoculated with *Schizochytrium* MTCC 5890 and fermentation was allowed to continue at a temperature of 30° C. under the condition of aeration 0.75-1 v/v/min and agitation 500 rpm, respectively. The *Schizochytrium* was isolated from Zuari-Mandovi mangroves, in Goa, India (S15°29'57.39",E73°52'6.13") near the Arabian Sea. During fermentation the pH value of the medium was maintained at about 7 by addition of sulphuric acid as required. Growth of *Schizochytrium* MTCC 5890 was monitored by determination of optical density (OD) at 600 nm using UV visible spectrophotometer (UV-2450, Shimadzu, Japan). Residual carbon substrate was measured by HPLC (Waters, USA) equipped with a refractive index detector fitted with an Aminex HPX-87H Column operated at 50° C. with $H_2SO_4$ as mobile phase. HPLC was calibrated by injecting standards of different concentrations. The calibration curve obtained for all the standards showed R2 value close to 0.998. The data are expressed in means of each set of experiments carried out in triplicates and the result given here is average of three independent samples.

This embodiment investigates the effect of specific ratio of potassium, magnesium, copper to nitrogen in modified minimal medium (MBM) for fast growth of starter/inoculum culture. The production medium mainly consists of acetate (30-40 g/L) as a substrate with all growth components, pH indicator and also supplemented with copper and specific ratios of potassium/nitrogen, magnesium/nitrogen to support the growth of Schizochytrium in enhancement of biomass and productivities.

Referring to FIG. 1A, B, C, the cell growth and acetate concentration were plotted against the incubation time. To devoid the use of yeast extract, peptone and seasalt in medium, the culture was grown in minimal medium (BM) wherein the growth of culture is found to be slow and showing extended lag phase (FIG. 1B) as compared to complex enriched medium (FIG. 1A). The cell concentration and acetate consumption rate improved significantly after modification of BM medium by adding copper and appropriate ratios of potassium and magnesium to nitrogen. Furthermore, short lag phase and fast acetate consumption exhibited enhancement in cell growth and rapid logarithmic phase in modified MBM medium. The maximum specific growth rate (u/day) obtained was 2.24/day in MBM followed by YPA medium (1.5/day) at 0.28 day whereas minimum specific growth rate (1.5/day) was observed in BM medium depicting that BM medium has inadequate growth nutrients for the culture. Based on the performance of the strain in presence of additional and appropriate quantities of essential nutrients in this experiment, the growth rate was improved by maximum 65% as compared to normal minimal medium (BM) without any additional salts in the medium.

Example 2: Determination of Growth Kinetics and Optimum Substrate Concentration in Modified Minimal Base Medium This example shows the effect of modified minimal media composition comprising of copper and specific ratios of potassium, magnesium to urea for the determination of range of substrate requirement in continuous media for rapid logarithmic phase and higher productivities. The nutrient media was mainly comprised under comparable conditions to Example 2. Batch experiments were carried out in four different parallel bioreactors (Biojenik Engineering, Chennai, India) with 2 L of modified medium, inoculated 10% v/v with a 24-h seed culture grown in minimal media 30 g/L acetate. The culture was kept at 30° C. and aerated with 0.75-1 v/v/min air; stirring was regulated in the range from 150 to 900 rpm to keep the dissolved oxygen at 20%. The medium pH, incubation temperature, time and agitation were 6.5-9.5, 30° C. at 120 hours respectively.

The determination of growth kinetics allowed the characteristics of the strains and to know about critical concentrations of substrate. In this experiment, the sub culturing was carried out from one reactor to another reactor at one particular time to confirm its lag period (time before growth commences), and the time at which the culture enters plateau (the period when cell number remains stable with time). The growth curves were used to establish the optimal substrate concentrations that are convenient and give a long exponential phase and high viable cell yield.

Referring to FIG. 2: The results obtained in this experiment showed that maximum substrate concentration 26 g/L or less, preferably 22 g/L or less, more preferably 18 g/L or less exhibited rapid logarithmic phase and reduced lag phase. The culture was showing plateau when the residual substrate was less than 8 g/L or less, preferably 4 g/L or less, more preferably 2 g/L or less. One point is noticeable herein that growth of the culture could not be inhibited with any range of substrate concentration.

Example 3: Determination of Optimal Growth Control Strategy

Residual substrate-controlled experiments have been done for describing both growth and substrate utilization in culture. In this regard, Schizochytrium MTCC 5890 growth kinetics has been investigated in four fed-batch systems with starting with different substrate concentrations i.e., 5 g/L-20 g/L. Using the fed-batch method, the acetate concentration was maintained at between 10 g/L and 15 g/L at 0.9th day in all the reactors. When the acetate was added by the fed batch method in the middle of the culture, sampling was done to know the exact concentration of substrate at that particular time. In this experiment, the consumption of the substrate and the increase in biomass concentration was monitored as a function of time.

Figure 3:
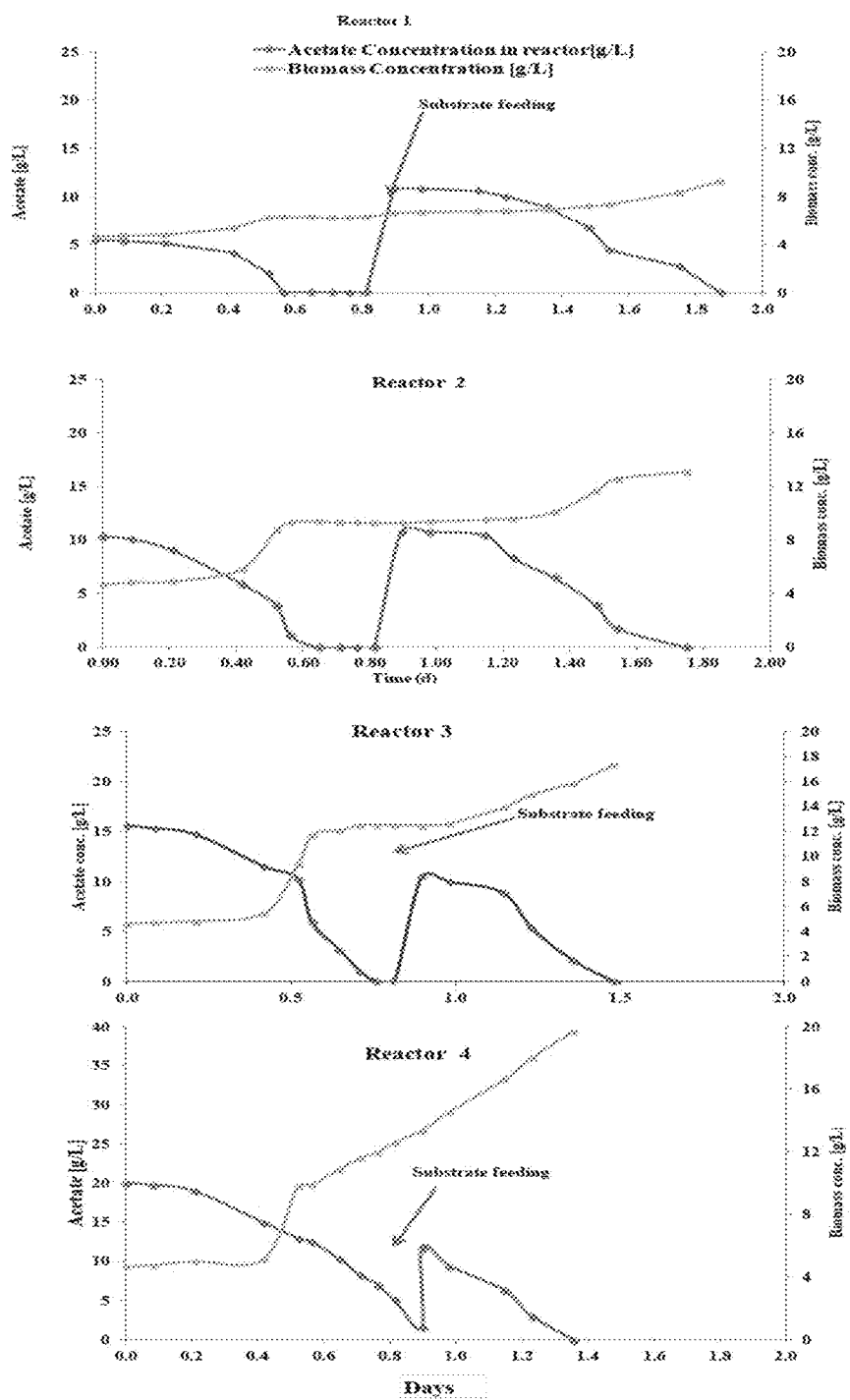
FIG. 3 illustrates the effect of different concentration of substrate on growth and productivity in fed batch cultures.

This example (FIG. 3) shows the effect of residual acetate on metabolic activity change in the culture during the experiment. It was observed that at lower initial substrate concentration (FIG. 3a), the stationary phase was reached at $0.5^{th}$ day during which no further growth occurred and culture was exposed to deep substrate starvation conditions. At $0.9^{th}$ day, when reactor was fed with 10 g/L acetate, culture took more time to regain their growth and showed extended lag phase in long term starved cells as compared to short term starved cells. The culture showed rapid logarithmic phase and faster growth in the presence of residual substrate. It was assumed that starvation of carbon source for longer time might have increased the chances of some of the cells to get lyses and exhibited the death phase. We showed that long term starved cells are growing and dividing, though it extended the lag phase and doubling time. However, in continuous culture, long term starved cells will be washed out of the fermentor, if the dilution rate exceeds the maximum specific growth rate. Thus, equilibrium concentration of the residual substrate is required which will allow the culture to grow at the set dilution rate by maintaining stable environmental growth conditions. Therefore, FIG. 3 shows more precise, reproducible data that can be used in continuous culture. The result showed that controlled band of residual substrate in a steady state continuous culture can be maintained in the range 14 g/L or less, preferably 10 g/L or less, more preferably 7 g/L or less to achieve maximum growth rate and productivity.

Example 4: Process for Obtaining Enriched Algal Biomass

For optimal productivity, fermentation is performed using modified medium under appropriate band of residual substrate in continuous fermentation to regulate the maximum productivities. These data monitor the growth rate of the culture for consistency and ensure that the culture is always fed at the optimal residual substrate concentrations.

Particularly, inoculum of Schizochytrium was prepared in modified media as discussed in Example 1 and incubated at 30° C., 200 rpm. 10% of 24 old inoculum was added in 2 L or 5Lt or 10 Lt Reactors half filled with modified production medium. Fermentor without supplemented media was kept as control. Two stainless steel tubes were installed in 2 L bioreactor for continuous media feeding and continuous culture harvesting (through overflow tube) by peristaltic pump. Bioreactor was made continuous with sterile media with starting feeding rate of 600-1200 ml d$^{-1}$. Feeding rate was gradually increased using unsterile media until culture started washing out to achieve maximum dilution and growth rate. Feeding was continued for next 60 days at higher dilution rate and media level was maintained across the cultivation period.

Culture was aerated with microspargers or with normal drilled pipe spargers. Culture was agitated with Rushton or pitch blade or marine impellers at 100-900 rpm maintain DO at 10% to 50% or more with combination of air and oxygen supply. Sample was taken regularly at the interval of 6 to 12 hour to determine nutrient sequestration, biomass production and lipid production. Effluent liquid streams were measured via HPLC with refractive index detector (RID) detection. Growth was monitored via OD600 and gravimetrically. Total lipids were quantified using a modified version of a lipid extraction protocol adapted from U.S. Pat. No. 9,890,402 B2 using gas chromatography-flame ionization detector (GCFID).

FIG. 4 exhibits the biomass and lipid productivity in modified medium supplemented with copper and specific ratio of K/N, Mg/N wherein control residual substrate concentration was maintained throughout the fermentation. In this experiment, modulation of specific band of residual substrate during long term continuous fermentation enhanced the acetate consumption rate and biomass productivity. Please refer to FIG. 4A, the culture showed the zig zag pattern of growth depending upon the fluctuations in residual substrate concentration in fermentor. Cells started bleed out when specific growth rate become less than dilution rate. We hypothesized that this might be due to starvation of carbon substrate and culture started washed out and when feeding increased, culture started to regain the growth with extended lag phase. Successful residual substrate control strategy for tuning of zig zag pattern was established by maintaining specific growth rate equal to dilution rate in a steady state. Based on the performance of selected isolate in presence of specific ratio of nutrients and specific band of residual substrate, the biomass productivity and acetate consumption rate were improved by maximum 2-3-fold as compared to control normal fermentation condition when no modified medium and control strategy of residual substrate concentration was provided.

Referring to FIGS. 4B and 4C, the specific productivity of lipid enriched with omega-3-fatty acids is about two-four times which achieved on control fermentor without supplemented media and applied strategy. On the other hand, much higher cell densities can be supported by switching to specific band of residual substrate concentrations in a steady state. The maximum acetate consumption rate, biomass and lipid productivity obtained was 130-140 g/L/d, 80-90 g/L/day and 20-30 g/L/day, respectively. The above yield was also better than the yield obtained by organisms in normal fermentations reported in previous literature studies.

Thus, the present invention provides a cost-effective and sustainable method of producing high biomass and lipid productivity by allowing the cells to incubate and grow faster in selected composition, whereby the potential of the culture to provide a biofuel product and other high value co products are enhanced compared to when the culture is not contact with the composition. A continuous steady state fermentation process has been established for a long time period (several weeks or months) at a faster dilution rate so that unproductive time would be minimal and also allow for the easier introduction of process automation. This process will be beneficial for addressing and reducing the cost of production of lipid enriched biomass and increases the economic viability of biofuels production and can also enhance the profitability of various nutraceutical and pharmaceutical industries.

We claim:

1. A process for production of enriched algal biomass having high lipid productivity, the process consisting of:
   i. providing an active starter culture of a microalgal strain;
   ii. inoculating 10% v/v of the microalgal strain of step (i) in a nutrient medium in a fermentor with a substrate, wherein the nutrient medium consists of potassium ions in a range of 5-150 mM, magnesium ions in a range of 4-10 mM, copper ions in a range of 0.4-0.9 mM, calcium ions in a range of 0.3-0.9 mM, sulphate ions in a range of 5.6-15 mM, urea in a range of 14-40 mM, trace elements selected from the group consisting of $FeCl_3$, $CoCl_2$, $H_3BO_3$, $Na_2MoO_4$, $ZnCl_2$, and $Na_2WO_4$, and vitamins selected from the group consisting of biotin, folic acid, pyridoxine HCl, thiamine HCl, riboflavin, nicotinic acid, B12, and thioctic acid;
   iii. fermenting the nutrient medium of step (ii) at a temperature ranging from 20-37° C. at an aeration of 0.75-1 v/v/min and regulating stirring in a range from 150 to 900 rpm to keep dissolved oxygen at 20% throughout a continuous run;
   iv. maintaining a pH value of the nutrient medium of step (iii) in a range of 6.5-9.5 and a concentration of a residual substrate in a range of 4-15 g/L inside the fermentor;
   v. allowing the active starter culture to grow in a logarithmic phase in a steady state continuous run; and
   vi. obtaining algal biomass enriched with omega-3 containing lipids from the fermentor.

2. The process as claimed in claim 1, wherein the microalgal strain is *Schizochytrium* MTCC 5890.

3. The process as claimed in claim 1, wherein the substrate is acetate.

4. The process as claimed in claim 3, wherein the acetate is used in a concentration of 30-40 g/L.

5. The process as claimed in claim 1, wherein the nutrient medium is a modified minimal base medium.

6. The process as claimed in claim 1, wherein the pH value of the nutrient medium is maintained by adding sulphuric acid.

7. The process as claimed in claim 1, wherein the lipid productivity is in a range of 20-30 g/L/day and the obtained biomass is in a range of 80-90 g/L/day.

8. The process as claimed in claim 1, wherein in the nutrient medium K/N:Mg/N:Cu/N are in a ratio of 0.349:0.109:0.023.

* * * * *